United States Patent [19]
Werle et al.

[11] Patent Number: 5,917,094
[45] Date of Patent: Jun. 29, 1999

[54] ACROLEIN-RELEASING EMULSION HOMOPOLYMERS

[75] Inventors: Peter Werle, Gelnhausen; Hans Peter Krimmer, Dietzenbach; Martin Trageser, Gelnhausen, all of Germany

[73] Assignee: Degussa-Hüls Aktiengesellschaft, Frankfurt am Main, Germany

[21] Appl. No.: 08/991,205

[22] Filed: Dec. 16, 1997

[30] Foreign Application Priority Data

Dec. 20, 1996 [DE] Germany .............. 196 53 305

[51] Int. Cl.$^6$ .............. C07C 45/47; A01N 35/02
[52] U.S. Cl. .............. 568/449; 526/315; 422/36; 514/703; 568/421
[58] Field of Search .............. 526/315; 424/78.08, 424/78.37; 568/420, 421, 449; 422/36; 514/703

[56] References Cited

U.S. PATENT DOCUMENTS

| | | | |
|---|---|---|---|
| 3,936,423 | 2/1976 | Randazzo | 260/67 |
| 4,058,608 | 11/1977 | Zsolnai et al. | 424/226 |
| 4,783,336 | 11/1988 | Margel et al. | 424/462 |

FOREIGN PATENT DOCUMENTS

| | | |
|---|---|---|
| 1565846 | 5/1990 | U.S.S.R. |
| 88 04671 | 6/1988 | WIPO . |
| 96 38186 | 12/1996 | WIPO . |

*Primary Examiner*—Gary Geist
*Assistant Examiner*—S. Padmanabhan
*Attorney, Agent, or Firm*—Smith, Gambrell & Russell, LLP

[57] ABSTRACT

Acrolein-releasing emulsion homopolymers release acrolein in aqueous systems. They are produced by adding acrolein, at least 95% by weight pure, to a solution of an alkali hydroxide, with the temperature not exceeding 25° C. during the addition, and then adjusting the pH to 5 to 7 by adding a mineral acid.

13 Claims, 3 Drawing Sheets

ACROLEIN-RELEASING EMULSION HOMOPOLYMERS

INTRODUCTION AND BACKGROUND

The present invention relates to acrolein-releasing emulsion homopolymers, the process for producing them, and their use as biocides.

It is known that monomeric acrolein (2-propenal) is a very effective biocide for use in treating waterways to suppress undesired algal and plant growth. It can also be used against sulfate-reducing bacteria in petroleum exploration.

Other areas of application for the biocidal action of monomeric acrolein have not yet appeared because of its high reactivity. For instance, studies have shown that acrolein is subject to rapid alterations in aqueous systems, such as hydration or polymerization, depending on the pH (see FIG. 1). For that reason it has not been possible in the past to use acrolein as a preservative with long-lasting action. Because of its tendency to polymerize spontaneously, and sometimes explosively, with unexpert handling, it can be handled only by utilizing special safety procedures. It has a strong irritating action on the respiratory organs and the eyes. Acrolein has only limited storability even in the stabilized form.

It is known that copolymers of acrolein and formaldehyde can be made through condensation of acrolein and formaldehyde at molar ratios from 1:1 to 1:10 in the presence of a basic catalyst, and that they can be used as biocides for aqueous systems (German Patent Application B 32 05 484). The known copolymers of acrolein with formaldehyde have the disadvantage that they contain about 15% free unreacted formaldehyde.

Acrolein homopolymers are also known for use as biocides (European Patent Application 0 339 044). The polymerization is done predominantly by a free-radical process. The resulting polyaldehyde structures produced are supposed to be the carriers of the biocidal action. It is a disadvantage of the acrolein homopolymers produced by the free-radical process that they are not soluble in organic media or in water. Moreover, in the form of an aqueous suspension, they have only a very low biological activity.

The production of polyacroleins described in German Patent Application P 44 04 404 is problematic, because the yields from the reaction of acrolein with NaOH in an aqueous system are only 75–80% polymeric material. Therefore the mother liquor and wash water contain organic materials and must be disposed of at high cost. Recycling is impossible because of its bad effect on the polymer properties. These polymers, too, are nearly insoluble in water.

Acrolein polymers or copolymers which serve as sources of acrolein have not previously been described. The monomeric acrolein which is released continuously at low concentrations under suitable conditions should be a biocidal agent which is produced over a long period from the polymer or copolymer.

Emulsion polymers of acrolein have themselves been known for a very long time. H. Cherdon et al. describe production of emulsion polymers of acrolein using polyacrolein-$SO_2$- solutions as the emulsifier (in Makromolekulare Chem. 32, 197 (1959)).

Margel and Wiesel published the production of analogous products with defined particle sizes in, among other places, the Journal of Polymer Science, Polymer Chemistry Edition, Vol. 22, 145 (1984), and in U.S. Pat. No. 4,783,336. The polymerization is carried out under alkaline conditions with sodium hydroxide, or free radical polymerization with persulfate/silver as the catalyst. Use as a marker for cell determinations or in transmission electron microscopy is also mentioned.

European Patent Application 0 441 468 A2 describes the use of microparticles based on polyaldehydes, for example, as contrast agents.

Therefore an object of the invention is to provide an effective biocide agent for use in many applications which avoids prior art problems dealing with acrolein.

A further object of the invention is to produce acrolein homopolymers which have good biocidal activity and which can be handled simply.

SUMMARY OF THE INVENTION

The above and other objects of the invention are achieved by acrolein homopolymers which release acrolein in a controlled manner; and more particularly by releasing acrolein in aqueous systems at a pH greater than 7, thus exhibiting a biocidal action.

A feature of the invention resides in a process for producing acrolein-releasing emulsion homopolymers, characterized by the fact that acrolein, preferably of at least 95% by weight purity, is added to a solution of aqueous alkali hydroxide which may contain an emulsifier or a wetting agent, with the temperature being maintained at a maximum of 25° C. during the addition, followed, if desired, by further stirring, and neutralization, i. e., adjusting the pH of 5 to 7, by adding aqueous mineral acid. Hydrochloric acid can be used as the mineral acid. Sodium hydroxide can be used as the alkali hydroxide.

BRIEF DESCRIPTION OF DRAWINGS

The present invention will be further understood with reference to the drawings, wherein.

DETAILED DESCRIPTION OF DRAWINGS

According to the present invention, it has been found that emulsion homopolymers of acrolein produced according to the invention release acrolein at low concentrations and over a long period, so that they are suitable for preservation of many industrial products. Sodium sulfosuccinate esters are used preferably as emulsifiers to produce stable, milk-like emulsions.

The acrolein homopolymers produced according to the invention can have a mean particle size of 450 to 600 nm, preferably about 500 nm.

A further feature of the invention is a process for preserving materials, by the addition of the emulsion polymer to the materials as compounds which release acrolein.

For instance, the following materials can be preserved according to the invention:

Plastic dispersions, disinfectant solutions for use on wood, building facings, and walls; paints, pigment formulations and pastes, sealing compounds, calcimines, protective coatings for wood, adhesive emulsions, hide and leather glues, bone glues, starch glues, casein glues, dextrin glues, salted hides, pickling solutions, dry hides, tanners' liquors, wet chrome leather, finished leather, spinning baths, wax emulsions, wax raw materials, textile finishes, textile dressings, paper/cardboard, PVC- and cutting oils (preserved), wood preservation, cellulose fibers (protection against dry rot), sealing cement, marine paint, and liquid cleaning agents.

The acrolein polymers according to the invention can be added to the materials in proportions of 0.005–0.3% by weight.

Figure 1:
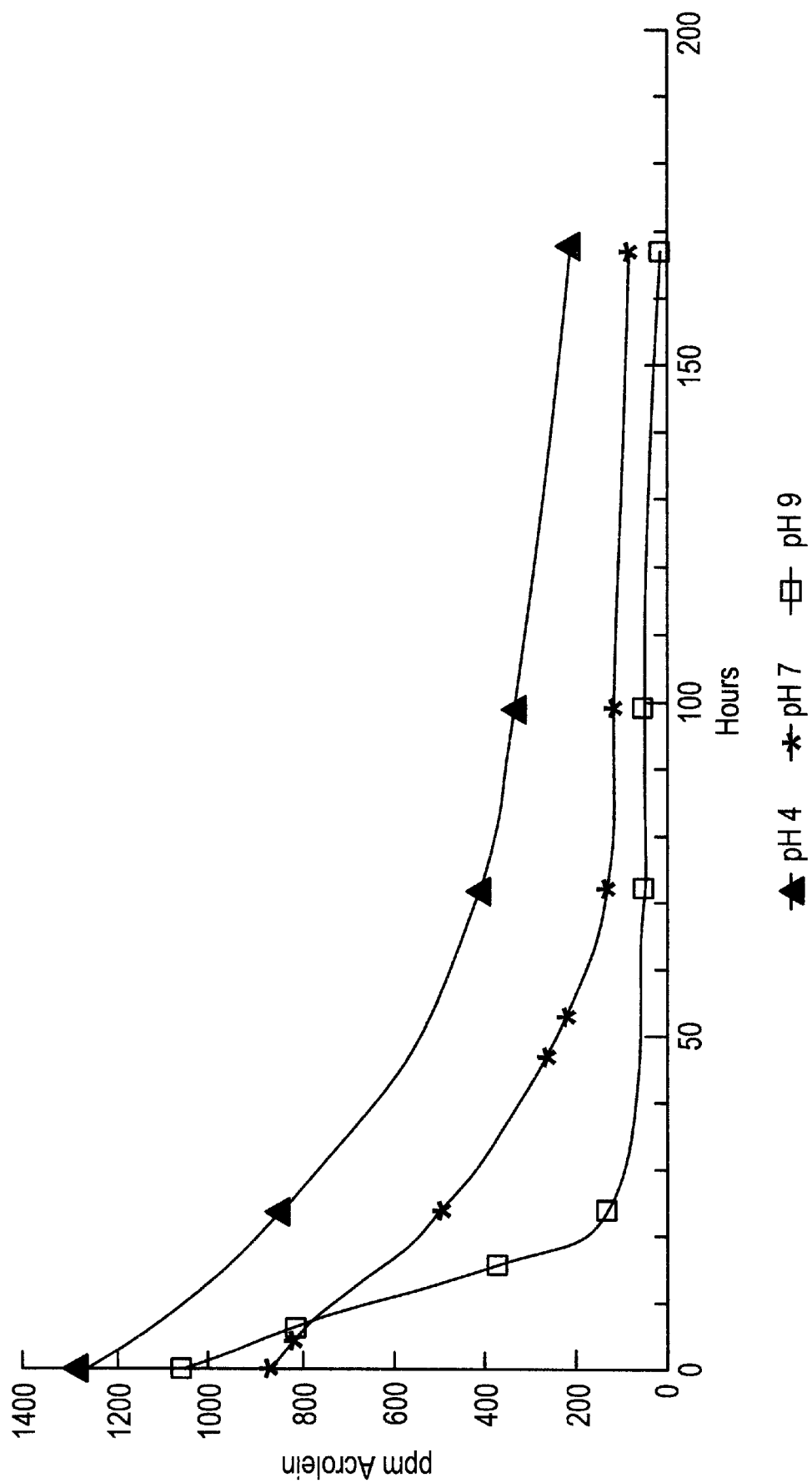
FIG. 1 is a graph of the relationship between acrolein content in an aqueous solution at various pH values over a period of time.
Figure 2:
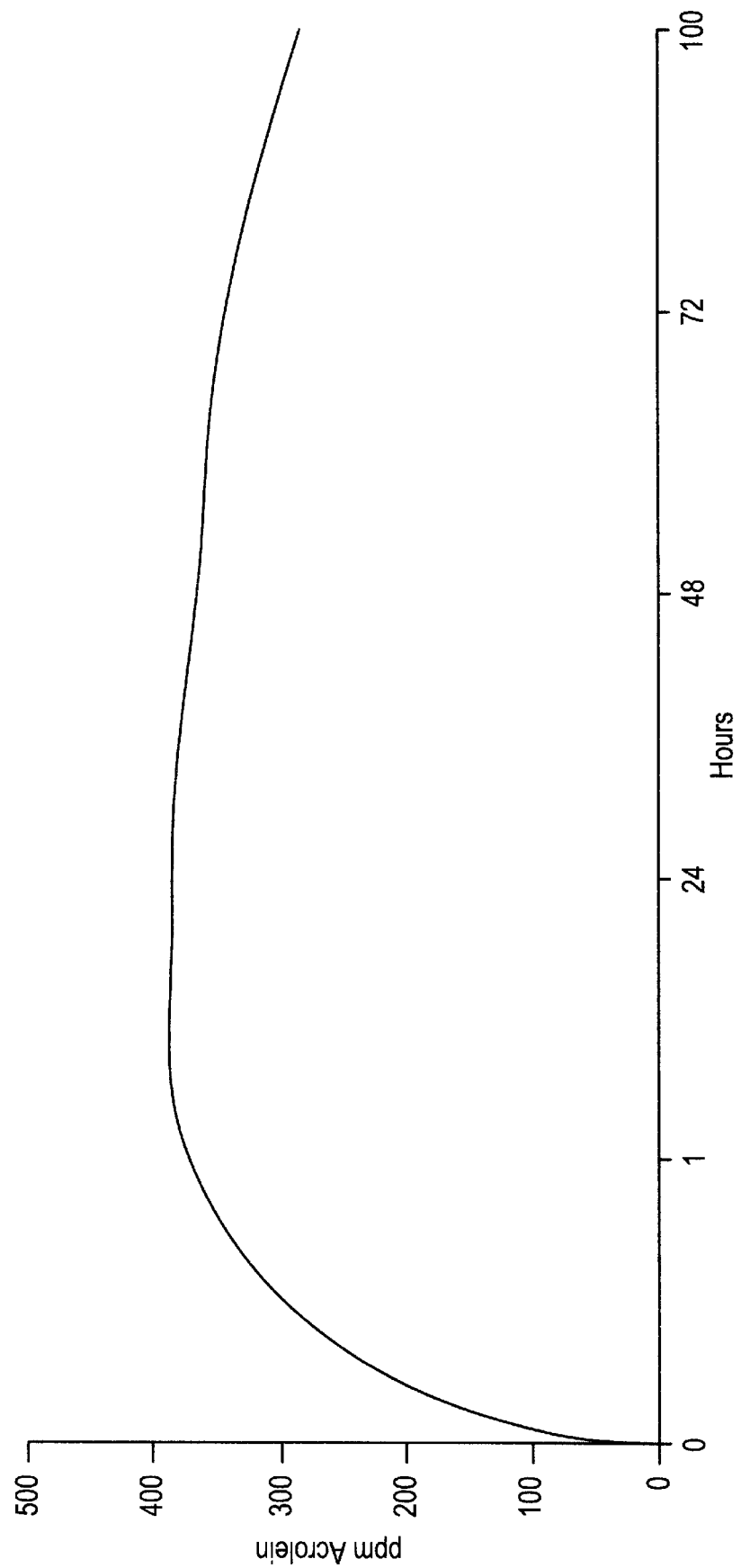
FIG. 2 is a graph representing the decomposition of a 2% acrolein polymer composition of Example 2 in a buffered solution at a pH of 9 over time.

As these emulsion polymers are only slightly soluble in water, they are not useful by themselves as quick-acting disinfectants. But the slow, continuous release of acrolein, especially at elevated pH, provides excellent preservative action. FIG. 1 shows the effect of pH on release of acrolein over a period of many hours. FIG. 2 shows acrolein release over time in hours in buffered solutions at pH 9. This finding is surprising and unforeseeable, as the literature teaches that acrolein polymerizes spontaneously at these pH values, so that release of monomeric acrolein is not to be expected.

EXAMPLES

Example 1

270 ml water, 1.2 ml 1N sodium hydroxide and 0.3 ml emulsifier (Rewopol SDB 075) are mixed at room temperature. Over a period of one hour, 36 ml of approximately 95% acrolein is added dropwise, with cooling. Stirring is continued for another hour at room temperature, and the mixture is neutralized by addition of 1.2 ml 1N hydrochloric acid.

Yield: about 300 g of 10% acrolein polymer emulsion with a particle size, $d_{50}$, of about 500 nm.

being tested are weighed and homogeneously mixed in. An unpreserved sample of paint is used as a control.

The sample beakers are stored in a low-temperature incubator at 25° C. and 65% relative humidity during the rest period. Three days after addition of the preservative, the samples are inoculated with a mixture of bacteria made up of approximately equal parts of *Alcaligenes denitrificans, E. coli, Klebsiella pneumoniae, Proteus mirabilis, Proteus vulgaris, Pseudomonas aeruginosa, Pseudomonas putida, Serratia marcescens* and *Staphylococcus aureus* and stirred with a spatula. The inoculation is done for a total of seven times at weekly intervals. After thorough mixing of the sample beakers, samples are taken after 3 and 7 days and streaked on CASO agar. The streaks are examined after incubation for three days at 25–30° C. Negative streaks are observed two more days to make sure and examined again.

Growth is evaluated according to the following plan:

0 no bacteria

0–1 up to 10 bacteria or colony-forming unit (CFU)

1 up to 30 bacteria or CFU 2 up to 100 bacteria or CFU 3 up to 250 bacteria or CFU 3–4 up to 500 bacteria or CFU 4 up to 1000 bacteria or CFU 5 up to 85% of the smear overgrown 6 up to 100% of the smear overgrown, dense growth CFU=colony-forming unit

TABLE 1

| Week/Inoculation | 1 | 2 | 3 | 4 | 5 | 6 | 7 |
|---|---|---|---|---|---|---|---|
| Streaks | 3d | 3d | 3d | 3d | 3d | 3d | 3d |
|  | 7d | 7d | 7d | 7d | 7d | 7d | 7d |
| Titer: CFU/ml | $2.7 \cdot 10^7$ | $4.2 \cdot 10^7$ | $3.7 \cdot 10^7$ | $4.0 \cdot 10^7$ | $4.0 \cdot 10^7$ | $4.0 \cdot 10^7$ | $5.9 \cdot 10^7$ |
| Date | 14 Nov 1995 | 21 Nov 1995 | 28 Nov 1995 | 5 Dec 1995 | 12 Dec 1995 | 19 Dec 1995 | 3 Jan 1996 |
| O-probe | 3–4 | 4 | 6 | 6 | 6 | 6 | 6 |
|  | 2 | 4 | 6 | 6 | 6 | 6 | 6 |
| Polymer from Example 1 0.01% | 0 | 0 | 0 | 0 | 0 | 0 | 0 |
|  | 0 | 0 | 0 | 0 | 0 | 0 | 0 |
| Polymer from Example 2 | 0 | 0 | 0 | 0 | 0 | 0 | 0 |
|  | 0 | 0 | 0 | 0 | 0 | 0 | 0 |

Example 2

1.80 liters of water, 12 ml 1N sodium hydroxide and 12 ml Rewopol SBD 075 are mixed. 1.44 liters of approximately 95% acrolein is added, with the mixture cooled by brine to a reaction temperature of 5–20° C. Stirring is continued for one hour at room temperature. The mixture is neutralized with 12 ml 1N hydrochloric acid.

Yield: about 3.0 kg 40% acrolein polymer emulsion.

The effectiveness of the emulsion polymer according to the invention can be demonstrated convincingly in a preservative challenge test.

Preservative challenge test 50 g of an unpreserved, freshly prepared latex paint is placed in a 100 ml polyethylene beaker. The substances Solutions used Example 2: 2% polymer in pH 9 buffer solution from Merck.

Tabulated measurements

| Residence time [hours] | Acrolein released [ppm] Example 2 |
|---|---|
| 0 | 0 |
| 1 | 370 |
| 24 | 385 |
| 48 | 365 |

-continued

| Residence time [hours] | Acrolein released [ppm] Example 2 |
|---|---|
| 72 | 342 |
| 100 | 284 |

These values are presented graphically in FIG. 2.

Figure 3:
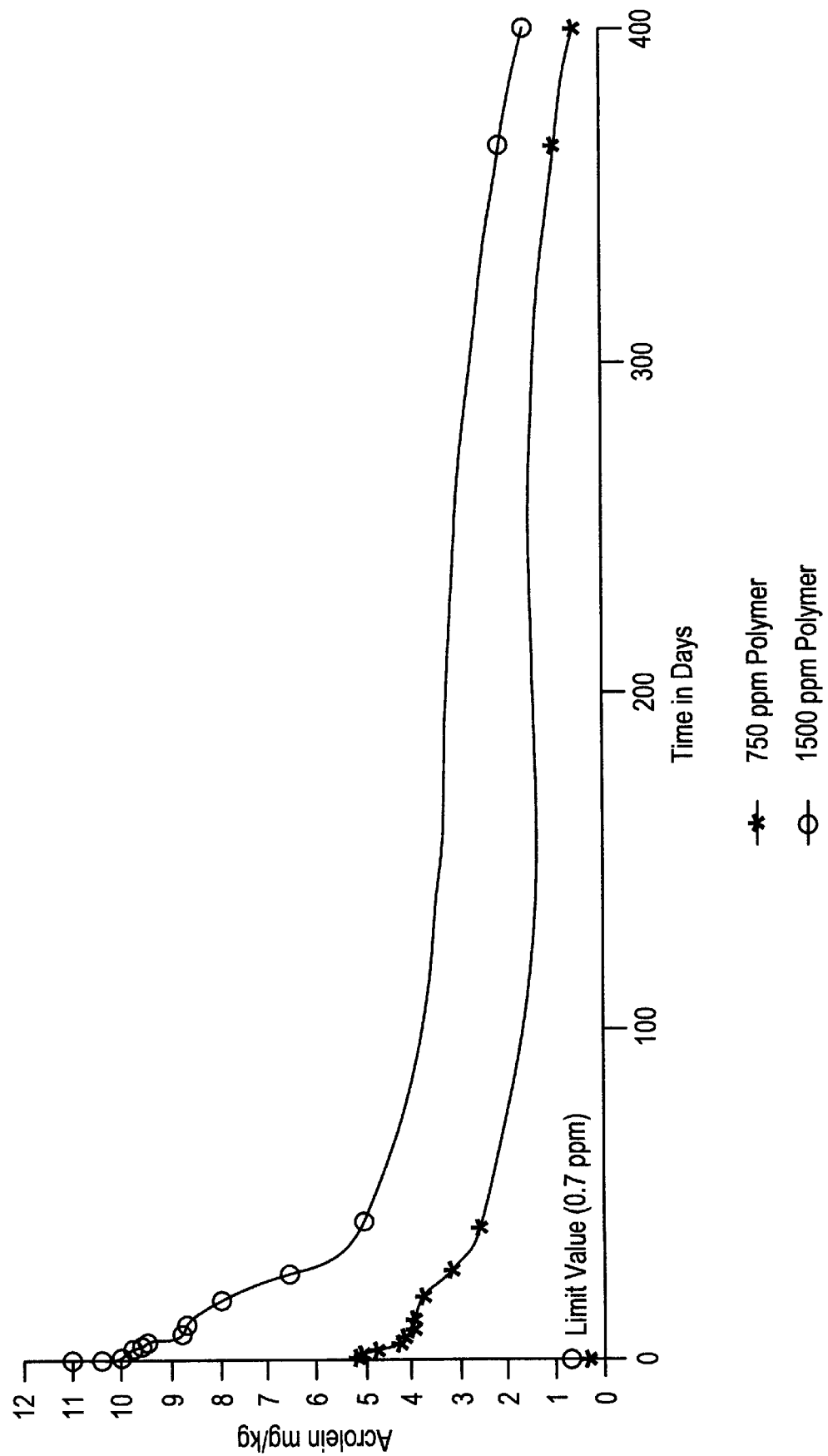
FIG. 3 is a graph of the acrolein content of a dispersion color preserved with the acrolein polymer of example 2 at a pH of 8.5, stored at room temperature over a long period of time, measured in days.

When a latex paint was preserved with 750 or 1500 ppm of an emulsion polymer produced as in Example 2, the content of free acrolein in the paint vehicle could be determined by HPLC, after separation of the paint solids, over a period of one year. The content is in the range of 1–2 ppm over a very long period (see FIG. 3). Preservative challenge tests, as described above, done in parallel with this test, showed complete killing of the added bacteria as long as the content of free acrolein was greater than about 0.7 ppm. In the case of preservation with 750 ppm homopolymer, reduction of the biological activity is found after more than 360 days, correlated with a free acrolein content of 0.7≦ ppm.

This gives rise to the unforeseeable and surprising conclusion that acrolein, if provided permanently from a source, is able to suppress bacterial cultures effectively in the sub-ppm range. Acrolein has not previously been considered to have such high activity, because when it is only added once it is quickly used up (water addition, dimerization), so that it is inactivated after only a few hours. Maintenance of a constant concentration of 1–2 ppm free acrolein by adding the polymer according to the invention, on the other hand, provides long-term preservation.

Further variations and modifications of the foregoing will be apparent to those skilled in the art and are intended to be encompassed by the claims appended hereto.

German priority application 196 53 305.8 is relied on and incorporated herein by reference.

We claim:

1. An acrolein-releasing emulsion homopolymer, characterized by the fact that it releases acrolein in aqueous systems at a pH greater than 7, thus exhibiting a biocidal action.

2. A process for producing the acrolein-releasing emulsion homopolymer according to claim 1, comprising mixing acrolein and a solution of aqueous alkali hydroxide, optionally containing an emulsifier or a wetting agent, to form a polymerization system, maintaining the temperature at a maximum of 25° C. during mixing of acrolein and the alkali hydroxide, optionally stirring, and neutralizing said polymerization system by adjusting the pH to 5 to 7 by adding an aqueous mineral acid.

3. The process according to claim 2 wherein said acrolein is 95% by weight pure.

4. The process according to claim 2 wherein an emulsifier is present which is sodium sulfosuccinate ester.

5. The process according to claim 2 wherein an acrolein homopolymer is produced wherein said homopolymer has a mean-particle of 450 to 600 nm.

6. The process according to claim 2 wherein the mineral acid is hydrochloric acid.

7. The process according to claim 2 wherein the alkali hydroxide is the sodium hydroxide.

8. The process according to claim 2 wherein said acrolein is added to a solution of aqueous alkali hydroxide.

9. An acrolein releasing homopolymer produced by the process of claim 2.

10. A process for preserving a material, comprising adding the emulsion homopolymer according to claim 1 to the materials to be preserved as an acrolein-releasing compound.

11. The process according to claim 10 wherein the amount of emulsion homopolymer added is 0.005% to 0.3% by weight of the material.

12. The process according to claim 2 wherein an emulsifier is present in the solution containing acrolein and aqueous alkali hydroxide.

13. The process according to claim 2 wherein a wetting agent is present in the solution containing acrolein and aqueous alkali hydroxide.

* * * * *